United States Patent [19]

Nielsson et al.

[11] Patent Number: 6,031,082
[45] Date of Patent: Feb. 29, 2000

[54] INCREASED YIELDS OF A CRYSTALLIZED PROTEIN BY USING A SOLID ADSORPTION MATERIAL

[75] Inventors: Stig Nielsson, Lynge; Niels Murmann, Lyngby, both of Denmark; Curran Simpson, Youngsville, N.C.

[73] Assignee: Novo Nordisk A/S, Bagsvaerd, Denmark

[21] Appl. No.: 09/141,740

[22] Filed: Aug. 27, 1998

Related U.S. Application Data

[63] Continuation of application No. PCT/DK97/00095, Mar. 3, 1997.

[30] Foreign Application Priority Data

Mar. 14, 1996 [DK] Denmark .................................. 0295/96

[51] Int. Cl.⁷ ................................ A23J 1/00; C07K 1/00
[52] U.S. Cl. ......................... 530/413; 530/415; 530/416; 530/417; 530/418
[58] Field of Search ...................................... 530/412, 413, 530/415, 416, 417, 418

[56] References Cited

U.S. PATENT DOCUMENTS 3,966,702   6/1976   Carey .
4,104,125   8/1978   Takechi et al. .......................... 435/206

FOREIGN PATENT DOCUMENTS 729208      5/1955    United Kingdom .
WO 94/22903 10/1994   WIPO .
WO 95/01989  1/1995   WIPO .

OTHER PUBLICATIONS

Ollis et al. (1990) "Protein Crystallization" Methods In Enzymology 182:648–659.

Judge et al. (1995) "Protein Purification by Bulk Crystallization: The Recovery of Ovalbumin" Biotechnology and Bioengineering 48:316–323.

*Primary Examiner*—Nathan M. Nutter
*Attorney, Agent, or Firm*—Steve T. Zelson, Esq.; Reza Green, Esq.

[57] ABSTRACT

The invention deals with a method for crystallizing in increased yields a polypeptide or a protein obtained from a protein solution comprising more than one protein, comprising:

(a) treating the protein solution with a solid adsorption material; and (b) crystallizing the polypeptide or the protein after said solid adsorption material has been removed; or (c) crystallizing the polypeptide or the protein without removing said adsorption material.

17 Claims, No Drawings

INCREASED YIELDS OF A CRYSTALLIZED PROTEIN BY USING A SOLID ADSORPTION MATERIAL

CROSS-REFERENCE TO RELATED APPLICATIONS

This application is a continuation of PCT/DK97/00095 filed Mar. 3, 1997 which claims priority under 35 U.S.C. 119 of Danish application 0295/96 filed Mar. 14, 1996, the contents of which are fully incorporated herein by reference.

TECHNICAL FIELD

The present invention relates to a simple, inexpensive and very effective method for crystallizing in increased yields a polypeptide or a protein, in particular an enzyme obtained from a fermentation broth.

BACKGROUND ART

Enzymes are usually provided as liquids or amorphous materials for industrial purposes. When not provided as liquids, they are usually provided as amorphous materials, because the known methods for crystallization of enzymes are usually regarded as too expensive to be used in an industrial scale.

There is an abundance of literature concerning crystallization of enzymes. It is difficult to generalize in respect to the outcome of specific crystallization procedures, as the art of enzyme crystallization is highly empirical.

Characteristic features of most of the hitherto known protein crystallization processes are: Pure and concentrated initial solutions, very long crystallization time, and high consumption of chemicals such as salts, for reference see, e.g., *Biotechnology and Bioengineering* 48, 1995, p. 316–323.

Industrial enzyme crystallization processes using polyethylene glycol have been described, for reference see WO 95/01989.

It has also been described that it is possible to crystallize enzymes by leaching out salts from the solution, followed by adjustment of the pH of the solution to a level around the pI of the enzyme, for reference see WO 94/22903.

It is known that solid adsorption materials such as active carbon is efficient in removing colour but it has not been described previously that such adsorption materials have a profound effect on polypeptide/protein crystallizations.

SUMMARY OF THE INVENTION

In this invention it is surprisingly found that a carbon treatment prior to or especially simultaneously with a protein crystallization process increases the crystallization yield and crystallization purity significantly.

Accordingly, the present invention provides a method for crystallizing in increased yields a polypeptide or a protein obtained from a protein solution comprising more than one protein, comprising:

(a) treating the protein solution with a solid adsorption material; and (b) crystallizing the polypeptide or the protein after said solid adsorption material has been removed; or (c) crystallizing the polypeptide or the protein without removing said adsorption material.

DETAILED DISCLOSURE OF THE INVENTION

The present invention provides a method for crystallizing in increased yields a protein or a polypeptide from a protein solution, in particular from a fermentation (culture) broth.

A fermentation broth contains besides the polypeptide or the protein of interest many other compounds such as substrate compounds, e.g., carbohydrates and salts, cells, and other metabolites such as nucleic acids and other polypeptides and proteins than the one of interest.

Preferably the method of the invention is applied to a fermentation broth that has first been subjected to solid/liquid separatory techniques, e.g., flocculation, centrifugation, filtration, micro filtration, ultrafiltration, precipitation, evaporation, or any combination thereof.

As the method of the invention works very well on relatively impure solutions, it will normally not be necessary to purify the protein solution obtained from the fermentation broth by use of chromatographic methods before the treatment with the solid adsorption material.

In a more specific embodiment, the method of invention comprises concentration of the protein containing solution by methods known per se. Such methods include concentration by ultrafiltration, by diafiltration, by dialysation, or by evaporation.

Concentration of the protein containing solution, although not essential for carrying out the treatment with the solid adsorption material, is convenient from a handling and a yield perspective. For practical reasons the protein containing solution may be concentrated to a content of proteins of from 0.1 to 25% w/w, preferably of from 0.5 to 15% w/w, in particular of from 1 to 10% w/w.

The method of the invention may be applied to any crystallization process known in the art, e.g., to a salt crystallization, to a crystallization using a polymer as disclosed in WO 95/01989, or to a crystallization process using the principle of leaching out salts from the solution, followed by adjustment of the pH of the solution to a level around the pI of the enzyme, for reference see WO 94/22903. The last mentioned crystallization method is used in the Examples of the present invention.

In a preferred embodiment, the method of the invention is applied to crystallization of an enzyme, in particular an enzyme selected from the group consisting of proteases, peptidases, lipases, amylases, cellulases, xylanases, isomerases and oxidoreductases.

Proteases

Suitable proteases to be crystallized according to the present invention include any protease which may be a fermentation product from a cell such as a microorganism. Bacterial or fungal origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the tradenames Alcalase, Savinase, Primase, Durazym, and Esperase by Novo Nordisk A/S (Denmark), those sold under the tradename Maxatase, Maxacal, Maxapem and Properase by Gist-Brocades, those sold under the tradename Purafect and Purafect OXP by Genencor International, and those sold under the tradename Opticlean and Optimase by Solvay Enzymes.

Lipases

Suitable lipases to be crystallized according to the present invention include any lipase which may be a fermentation product from a cell such as a microorganism. Bacterial or fungal origin is preferred. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in BP 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be crystallized, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Gist-Brocades), Lipolase™ and Lipolase Ultra™ (Novo Nordisk A/S), and Lipase P "Amano" (Amano Pharmaceutical Co. Ltd.).

Amylases

Suitable amylases ($\alpha$ or $\beta$) to be crystallized according to the present invention include any amylase which may be a fermentation product from a cell such as a microorganism. Bacterial or fungal origin is preferred. Chemically or genetically modified mutants are included.

Amylases include, for example, $\alpha$-amylases obtained from Bacillus, in particular a special strain of *B. licheniformis*, described in more detail in British Patent Specification No. 1,296,839. Commercially available amylases are Duramyl™, Termamyl™, Fungamyl™ and BAN™ (available from Novo Nordisk A/S) and Rapidase™ and Maxamyl p™ (available from (Gist-Brocades).

Other useful enzymes are the CGTases (cyclodextrin glucanotransferases, EC 2.4.1.19) obtainable from e.g. Bacillus, Thermoanaerobactor or Thermoanaerobacterium.

Cellulases

In the present context, the term "cellulase" refers to an enzyme which catalyses the degradation of cellulose to glucose, cellobiose, triose and other cello-oligosaccharides.

In a preferred embodiment of the invention, the cellulase to be crystallized is an endoglucanase (EC 3.2.1.4), preferably a monocomponent (recombinant) endoglucanase.

Preferably, the cellulase is a microbial cellulase, more preferably a bacterial or fungal cellulase.

Useful examples of bacterial cellulases are cellulases derived from or producible by bacteria from the group consisting of Pseudomonas, Bacillus, Cellulomonas, Clostridium, Microspora, Thermotoga, Caldocellum and Actinomycets such as Streptomyces, Termomonospora and Acidothemus, in particular from the group consisting of *Pseudomonas cellulolyticus, Bacillus lautus, Cellulomonas fimi, Microspora bispora, Termomonospora fusca, Termomonospora cellulolyticum* and *Acidothemus cellulolyticus*.

A useful cellulase to be crystallized is an acid cellulase, which is derived from or producible by fungi from the group of genera consisting of Trichoderma, Myrothecium, Aspergillus, Phanaerochaete, Neurospora, Neocallimastix and Botrytis, in particular from the group consisting of *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum* and *Botrytis cinerea*.

Another useful cellulase to be crystallized is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium, in particular from the group consisting of *Humicola insolens, Fusarium oxysporum, Myceliopthora thermophila, Penicillium janthinellum* and Cephalosporium sp., preferably from the group of species consisting of *Humicola insolens*, DSM 1800, *Fusarium oxysporum*, DSM 2672, Myceliopthora thermophila, CBS 117.65, and Cephalosporium sp., RYM-202.

Other examples of useful cellulases to be crystallized are variants having, as a parent cellulase, a cellulase of fungal or bacterial origin, e.g. a cellulase derivable from a strain of the fungal genus Humicola, Trichoderma or Fusarium.

Oxidoreductases

Oxidoreductases which may be crystallized according to the invention include peroxidases, and oxidases such as laccases.

Peroxidases

An enzyme exhibiting peroxidase activity may be any peroxidase enzyme comprised by the enzyme classification (EC 1.11.1.7), or any fragment derived therefrom, exhibiting peroxidase activity.

Preferably, the peroxidase employed in the method of the invention is producible by microorganisms such as fungi or bacteria. Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus f. microsporus* (IFO 8371), *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g., *Streptomyces spheroides* (ATTC 23965), *Streptomyces thermoviolaceus* (IFO 12382) or *Streptoverticillum verticillium* ssp. verticillium.

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g., *M. virescens*.

Particularly, a recombinantly produced peroxidase is preferred, e.g., a peroxidase derived from a Coprinus sp., in particular *C. macrorhizus* or *C. cinereus* according to WO 92/16634, or a variant thereof, e.g., a variant as described in WO 94/12621.

Laccases and Laccase Related Enzymes

In the context of this invention, laccases and laccase related enzymes contemplate any laccase enzyme comprised by the enzyme classification (EC 1.10.3.2), any chatechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The microbial laccase enzyme may be derived from bacteria or fungi (including filamentous fungi and yeasts) and suitable examples include a laccase derivable from a strain of Aspergillus, Neurospora, e.g., *N. crassa*, Podospora, Botrytis, Collybia, Fomes, Lentinus, Pleurotus, Trametes, e.g., *T. villosa* and *T. versicolor*, Rhizoctonia, e.g., *R. solani*, Coprinus, e.g. *C. plicatilis* and *C. cinereus*, Psatyrella, Myceliophthora, e.g. *M. thermophila*, Schytalidium, Polyporus, e.g., *P. pinsitus*, Phlebia, e.g., *P. radita* (WO 92/01046), or Coriolus, e.g., *C. hirsutus* (JP 2-238885), in particular laccases obtainable from Trametes, Myceliophthora, Schytalidium or Polyporus.

Treatment with Adsorption Materials

We have surprisingly found that low concentrations of an adsorption material prior to or simultaneously with the crystallization process may increase the crystallization yield significantly, and at the same time increase the purity of the crystals formed and give the crystals a morphology which is easier to harvest as demonstrated in the enclosed Examples.

According to the invention any solid adsorption material known in the art may be used; an especially useful adsorption material is a carbon material, in particular an activated carbon material. The carbon material may be in the form of powder, granules, pellets or in any other form known in the art.

Useful activated carbon types may be Acticarbon 4S #2228, available from Elf Atochem North America, Darco carbon KB-B, available from American Norit Co., or Calgon granular carbon, available from Pittsburgh Activated Carbon.

Other solid adsorption materials which may be used according to the invention include diatomaceous earth (kieselguhr), fuller's earth, bentonite and various hydrophobic or ion-exchange resins.

It may in some cases be an advantage to add more than one adsorption material.

In a particular embodiment of the invention the solid adsorption material is added to the protein solution at a concentration of 0.05–5% w/w, preferably at a concentration of 0.1–2% w/w.

The solid adsorption material may be added in one step, or it may be added in more than one step; normally the process will perform satisfactorily when the solid adsorption material is added in one step.

The solid adsorption material treatment will normally last for a period of up to 40 hours, in particular for a period of ½ to 20 hours, preferably for a period of 1 to 10 hours, more preferably for a period of 1 to 5 hours, before it is removed prior to the crystallization, or if the solid adsorption material is in the solution while crystallizing it will be in the solution as long as the crystallization lasts, which may differ depending on the chosen crystallization method.

It may in some cases be an advantage first to add the adsorption material after the crystallization has started.

The chosen solid adsorption treatment time will depend on many factors such as product stability, the microbial level, and the capacity of the process equipment, but normally it will be for such a short period of time that it is not necessary to add any stabilizing agents or inhibitors to the protein solution.

The temperature of the protein solution treated with the solid adsorption material is preferably of from 5° C. to 50° C., in particular of from 10° C. to 40° C.

The pH of the protein solution treated with the solid adsorption material is preferably of from 3 to 10.

Instead of adding the solid adsorption material to the protein solution in the form of a powder, granules or pellets it may in some cases be an advantage to let the protein solution pass through a column filled with the adsorption material or let the proetin solution pass through, e.g., a carbon filter. This may be the case, e.g., in a salt crystallization process, where it may be an advantage first to add some of the salt, then let the protein solution pass through a carbon column or a carbon filter, and then add the remaining salt whereby the nucleation starts.

Crystallization

By using the method of the invention we have shown (see Example 2) that:

the crystallization yield is increased, the purity of the crystals are improved, the crystallization time for crystal formation is reduced, and the morphology of the formed crystals is changed.

Example 2 also shows that the effect of the solid adsorption material is biggest if the carbon is left in the concentrate during crystallization. Leaving the carbon in the concentrate is also production wise to prefer in order to reduce process time.

Recovery After Crystallization

The method of the invention causes the polypeptide or the protein, in particular the enzyme, to crystallize in a more pure form and at a higher yield.

If the solid adsorption material is left in the solution while crystallizing, the crystals will normally after harvest be redissolved and thereafter be the subject of a solid liquid separation process such as a filtration in order to remove insoluble matter like the adsorption material.

If crystalline products of a very high purity are desirable, the process of the invention may be repeated, i.e. the crystalline end product of the process of the invention is redissolved and subjected to one or more additional solid adsorption material treatments and/or crystallizations.

The end product may be a crystalline product or the crystals may be redissolved in order to produce e.g. a liquid polypeptide or protein product of high purity.

The invention is further illustrated in the following examples which are not intended to be in any way limiting to the scope of the invention as claimed.

EXAMPLE 1

Effect of Simultaneous Adsorption of Impurities by Carbon for Improving the Crystallization Performance of Lipase 100 Kg culture broth containing a *Humicola lanuginosa* lipase expressed in *Aspergillus oryzae* as described in EP 305 216, was pretreated as shown in Table 1 below.

TABLE 1

Pretreatment of Lipase Broth.

| | Pretreatment |
|---|---|
| Broth | 100 Kg |
| Water | 100 Kg |

The production strain was removed by drum filtration yielding a filtrate which successively was filtrated using Seitz K900 filter pads. Microbial count was reduced by filtration using Seitz EK1 filter pads. The resulting filtrate was concentrated on Dow DDS (20 kD) membranes. The UF-concentrate was further diafiltrated to a conductivity of 0.8 mS.

The purity of the resulting concentrate is illustrated by the ratio of ($mOD_{440\,nm}$/g active lipase).

TABLE 2

Purity of Concentrate Produced (before crystallization start).

| | $mOD_{440nm}$/g active lipase |
|---|---|
| UF-Concentrate | 104 |

The concentrate was subjected to various amounts of Acticarbon 4S #2228 and adjusted to pH=4.3 using a 20% w/w formic acid solution and left for 24 hours of crystallization time.

The crystal suspensions were harvested by centrifugation and the crystals washed using deionized water adjusted to pH=4.3 using formic acid. The crystal cakes were dissolved and formulated in 4 fold by weight of a 50% MPG+0.3% w/w $CaCl_2 \times 2H_2O$ solution and subjected to filtration using Seitz EK1 filter pads to remove carbon. The resulting formulated products were analyzed for $OD_{440\,nm}$ and lipase activity using tri-butyrin assay:

The tri-butyrin assay is based on the hydrolysis of tri-butyrin by the enzyme, and the alkali consumption is registered as a function of time. One Lipase Unit (LU) is defined as the amount of enzyme which, under standard conditions (i.e. at 30.0° C.; pH 7.0; with Gum Arabic as emulsifier and tri-butyrine as substrate) liberates 1 μmole titrable butyric acid per minute.

The yields and purities of the final products are shown in Table 3 below.

TABLE 3

UF-Concentrate subjected to increasing amounts of carbon and crystallized at pH = 4.3 and 28° C. showing yield, purity and morphology.

| | Yield of active lipase in formulated product | $mOD_{440nm}$/g active lipase in formulated product | Morphology |
|---|---|---|---|
| 0% w/w Carbon | 53% | 12.4 | Diamonds |
| 0.5% w/w Carbon | 64% | 7.2 | Rods |
| 1.0% w/w Carbon | 77% | 4.5 | Rods |

We find that both yield and purity is increased by using carbon during crystallization indicating that some impurities which inhibit crystallization of the lipase are removed.

The increase in purity is seen by the reduction of colour ($mOD_{440\,nm}$/g active lipase) in the formulated product. We also find a change in morphology towards rods (from diamonds).

In other words, this Example shows that by using the method of the invention we can increase the yield substantially and at the same time achieve a higher purity and a uniform rod shape of the enzyme crystals formed.

EXAMPLE 2

Effect of Pre-adsorption or Simultaneous Adsorption of Impurities by Carbon Treatment on Lipase Crystallization A UF-concentrate was obtained as described in Example 1. The UF-Concentrate was diafiltrated to a conductivity of 1.0 mS.

The purity of the resulting concentrate is illustrated by the ratio of ($mOD_{440\,nm}$/g active lipase) as shown in Table 4 below.

TABLE 4

Purity of Concentrate produced (before crystallization start).

| | $mOD_{440nm}$/g active lipase |
|---|---|
| UF-Concentrate | 42 |

The concentrate was divided into three fractions A, B & C and treated as shown in Table 5 below.

TABLE 5

The three fractions subjected to different treatments before crystallization start.

| | Treatment |
|---|---|
| Fraction A | No treatment |
| Fraction B | Added 0.5% Acticarbon 4S for 1 hour, at app. 20° C., then subjected to filtration using EK1 filter pads to remove carbon before crystallization |
| Fraction C | Added 0.5% Acticarbon 4S, and left in during crystallization |

The three fractions were subsequently adjusted to pH=4.3 and heated to 28° C. and left for 24 hours of crystallization time. The crystal suspensions were harvested by centrifugation and the crystals washed using deionized water adjusted to pH=4.3 using formic acid. The crystal cakes were dissolved and formulated in 4 fold by weight of a 50% MPG+0.3% w/w $CaCl_2 \times 2H_2O$ solution and then subjected to filtration using Seitz EK1 filter pads to remove carbon. The resulting formulated products were analyzed for $OD_{440\,nm}$ and lipase activity using tri-butyrin assay.

The yields and purities of the final products are shown in Table 6 below.

TABLE 6

Fraction A, B & C crystallized showing a better effect on both yield and purity when leaving carbon in the concentrate during crystallization.

| | Yield of active lipase in formulated product | $mOD_{440nm}$/g active lipase in formulated product | Time for visual crystal formation | Morphology |
|---|---|---|---|---|
| Fraction A | 84% | 9.4 | 3 hours | 80% diamonds 20% rods |

TABLE 6-continued

Fraction A, B & C crystallized showing a better effect on both yield and purity when leaving carbon in the concentrate during crystallization.

| | Yield of active lipase in formulated product | $mOD_{440nm}/g$ active lipase in formulated product | Time for visual crystal formation | Morphology |
| --- | --- | --- | --- | --- |
| Fraction B | 89% | 6.1 | 1 hour | 100% rods |
| Fraction C | 93% | 4.4 | 1 hour | 100% rods |

When comparing Fraction A with Fraction B or Fraction C it is seen that a carbon treatment prior to crystallization increases yield and purity, and that the effect is biggest if the carbon is left in the concentrate during crystallization. Leaving the carbon in the concentrate is also production wise to prefer in order to reduce process time.

It is also seen from Table 6 that we can control morphology from a mixture of crystal shapes to one uniform crystal shape by using the carbon treatment, so by using the method of the invention the yield is increased and the morphology is controlled.

EXAMPLE 3
Pilot Plant Scale Evaluation of Simultaneous Adsorption of Impurities by Carbon Treatment to Improve Crystallization Performance of Lipase A UF-concentrate was obtained in pilot plant scale in a similar way as described in Example 1. The UF-Concentrate was diafiltrated to a conductivity of 1.0 mS.

A laboratory test was conducted using increasing amounts of carbon (type Darco carbon KB-B) up to the amount used in a pilot plant scale trial as shown in Table 7 below.

TABLE 7

Combined Laboratory and Pilot scale trial of carbon treatment during crystallization.

| | % Carbon added | Yield of active lipase from formulated product | $mOD_{440nm}/$ g active Lipase of formulated product |
| --- | --- | --- | --- |
| Laboratory Control | 0% | 70% | 7.9 |
| Laboratory Test #1 | 0.5% | 77% | 6.1 |
| Laboratory Test #2 | 1.0% | 86% | 4.9 |
| Pilot scale test | 1.0% | 84% | 5.0 |

Table 7 indicates surprisingly good agreement between laboratory experiments and pilot scale results regarding both yield and purity. It is therefore possible directly to upscale laboratory results to a production plant process. Again a significant difference between carbon treatment and control is seen in the laboratory experiment.

EXAMPLE 4
Effect of Use of Granual Carbon in Simultaneous Adsorption of Impurities by Carbon Treatment to Improve Crystallization Performance of Lipase A UF-concentrate was obtained as described in Example 1. The UF-Concentrate was diafiltrated to a conductivity of 1.0 mS.

The purity of the resulting concentrate is illustrated by the ratio of ($mOD_{440\ nm}/g$ active lipase) as shown in Table 8 below.

TABLE 8

Purity of Concentrate produced (before crystallization start).

| | $mOD_{440nm}/g$ active Lipase |
| --- | --- |
| UF-Concentrate | 69 |

A Laboratory test was conducted using increasing amounts of a granular form of carbon (type Calgon) as shown in Table 9 below.

TABLE 9

UF-Concentrate subjected to increasing amounts of carbon and crystallized at pH = 4.3 and 28° C. showing yield and purity.

| | Yield of active lipase in formulated product | $mOD_{440nm}/g$ active lipase in formulated product |
| --- | --- | --- |
| 0% w/w Carbon | 75% | 7.1 |
| 1.0% w/w Carbon | 77% | 6.8 |
| 2.0% w/w Carbon | 87% | 5.8 |

It is seen from Table 9 that the yield is increased significantly and the purity is slightly increased using this granular form of carbon during crystallization.

EXAMPLE 5
Effect of Simultaneous Adsorption of Impurities by Carbon Treatment to Improve Crystallization Performance of Protease 100 Kg culture broth containing a *Bacillus lentus* protease, fermented e.g. as described in U.S. Pat. No. 3,723,250, was pretreated and flocculated as described in Table 10 below.

TABLE 10

Pretreatment and flocculation of protease broth.

| | Pretreatment & flocculation |
| --- | --- |
| Broth | 100 Kg |
| Water | 100 Kg |
| $CaCl_2 \times 2H_2O$ | 3 Kg |
| pH | pH adjusted to pH = 7.5 |
| 0.1% superfloc C521 | 1 Kg |
| 0.1% superfloc A130 | 1 Kg |

The production strain was removed by drumfiltration yielding a filtrate which successively was filtrated using Seitz K900 pads. Microbial count was reduced by filtration using Seitz EK1 filter pads. The resulting filtrate was concentrated on Asahi (6 kD) membranes, The purity is illustrated by the colour ($OD_{440\ nm}/g$ active protease) as shown in Table 11 below.

TABLE 11

Purity of UF-Concentrate before crystallization.

| | $OD_{440nm}/g$ active protease |
| --- | --- |
| Concentrate | 673 |

The UF-Concentrate was subjected to different amounts of FGV120 carbon and crystallized using 7% KAc and adjusted to pH=4.9 using a 20% w/w phosphoric acid solution. The crystallizations were carried out using a temperature ramp starting at 10° C. and ending at 28° C. after 5 hours. 24 hours was used as crystallization time.

The final crystals were harvested by centrifugation and the crystals washed using a 5.5% $CaCl_2$ (pH=4.9) solution. The crystal cakes were dissolved in 10 fold by weight of a 100% MPG solution and the resulting products were analyzed for $OD_{440\ nm}$ and protease activity by using a kinetic dimethyl casein assay:

The kinetic dimethyl casein assay is based on the digestion of a dimethyl casein solution by the proteolytic enzyme. The primary amino groups formed in this process react with trinitrobenzene sulphonic acid forming a coloured complex. The reaction is followed in situ in order that the change in absorbance per time unit can be calculated. The activity is determined relatively to an enzyme standard, and in the same units as for the standard.

The resulting yields and purities are shown in Table 12 below.

TABLE 12

Protease Concentrate subjected to increasing amounts of carbon during crystallization.

| | Yield of active protease in formulated product | $OD_{440nm}/g$ active protease in formulated product | Morphology |
|---|---|---|---|
| 0% Carbon | 89% | 96 | 10–15μ rods |
| 0.5% Carbon | 91% | 85 | 10–15μ rods |
| 1.0% Carbon | 93% | 90 | 10–20μ rods |

It is seen from Table 12 that increasing the carbon dosage increases the yields. The purity expressed by $OD_{440\ nm}/g$ active protease in the formulated product is slightly increased. The morphology is changed slightly by a small average increase in crystal size.

EXAMPLE 6

Effect of Simultaneous Adsorption of Impurities by Carbon Treatment to Improve Crystallization Performance of EG1 Humicola Cellulase 100 Kg culture broth containing a EG1 *Humicola insolens* cellulase expressed in *Aspergillus oryzae* was pretreated as shown in Table 13 below.

TABLE 13

Pretreatment of *Aspergillus oryzae* broth.

| | Pretreatment |
|---|---|
| Broth | 100 Kg |
| Water | 100 Kg |
| pH adjusted using 10% NaOH | 9.5 |

The production strain was removed by drum filtration yielding a filtrate which successively was germfiltrated using Seitz EK1 filter pads. The resulting filtrate was concentrated on Dow DDS (20 kD) membranes to a dry matter content of 22%. The UF-concentrate was further diafiltrated using 3 volumes of tap water and thereafter subjected to a carbon treatment using 3% Picatif FGV 120 Carbon at pH=5.5 for 2 hours at 30° C. The carbon was removed by filtration using Seitz K900 filterpads and Seitz EK1 filterpads. The resulting concentrate had a conductivity of 1.06 mS.

The purity of the resulting concentrate is illustrated by the ratio of ($OD_{440\ nm}/g$ active cellulose).

TABLE 14

Purity of concentrate (before crystallization starts).

| | $OD_{440nm}/g$ active Cellulase |
|---|---|
| Concentrate | 21.7 |

The concentrate was subjected to different amounts of Picatif FGV 120 Carbon and adjusted to pH=5.4 using a 20 w/w % formic acid solution and left for 24 hours at 28° C. (crystallization time).

The crystal suspensions were harvested by centrifugation. The crystal cakes were dissolved and formulated in 8 fold by weight of water and 0.1% sodium chloride and subjected to filtration using 0.45μ filters to remove carbon. The resulting formulated products were analyzed for $OD_{440\ nm}$ and cellulase activity. The cellulase activity is measured as S-CEVU (Stabilized Cellulase Viscosity Unit) and is determined using a carboxymethylcellulose, CMC, substrate. The endocellulase decomposes the CMC. The resulting reduction in viscosity is determined by a vibration viscosimeter. The reaction is carried out at pH=7.5 in a 0.1 M phosphate buffer at 40° C. for 30 minutes.

The yields and purities of the final products are shown in Table 15.

TABLE 15

Concentrate subjected to increasing amounts of carbon and crystallized at pH = 5.4 and 28° C. showing yield and purity.

| | Yield of active Cellulase in formulated product | $OD_{440nm}/g$ active Cellulase in formulated product |
|---|---|---|
| 0 w/w % Carbon | 8% | 19.7 |
| 0.5 w/w % Carbon | 23% | 19.1 |
| 1.0 w/w % Carbon | 44% | 19.2 |

We find, surprisingly, that yield is increased using carbon during crystallization even though the concentrate had been subjected to carbon treatment before crystallization. In other words, we can increase yield substantially and without loosing purity by using carbon during crystallization.

EXAMPLE 7

Effect of Simultaneous Adsorption of Impurities by Kiselguhr Treatment to Improve Crystallization Performance of a Lipase 50 kg culture broth containing a protein engineered variant of a *Humicola lanuginosa* lipase expressed in *Aspergillus oryzae* was pre-treated as shown in Table 16 below.

TABLE 16

Pretreatment of *Aspergillus oryzae* broth.

| | Pretreatment |
|---|---|
| Broth | 50 Kg |
| Water | 50 Kg |

The production strain was removed by drum filtration at pH=10.0 (adjusted with 13% NaOH), yielding a filtrate which successively was filtrated using Seitz K250 filter pads. The resulting filtrate was concentrated on Dow DDS (20 kD) membranes. The UF-concentrate was further diafiltrated to a conductivity of 2.5 mS/cm using 2 volumes of tap water.

The concentrate was subjected to various amounts of Hyflo Supercell kiselguhr and adjusted to pH=4.7 using a 10 w/w % phosphoric acid solution at 50° C. Temperature was increased by 3° C. every 30 min. until 28° C., and left at this temperature for a total of 22, hours of crystallization time.

The yields and crystal morphologies are shown in Table 17 below.

TABLE 17

UF-Concentrate subjected to increasing amounts of kiselguhr and crystallized at pH = 4.7 increasing temperature showing yield and morphology.

| | Yield of crystallized lipase | Morphology |
|---|---|---|
| 0 w/w % Hyflo Supercell | 58% | Single Rods |
| 1.0 w/w % Hyflo Supercell | 77% | Multiple rods attached to kiselguhr forming stars |

We find, surprisingly, that yield is increased using kiselguhr during crystallization. We also find a change in morphology towards stars from rods. In other words, we can increase yield and obtain a larger crystal form when using kiselguhr during crystallization.

We claim:

1. A method for obtaining crystals of a protein from a solution containing more than one protein, said method comprising:

(a) treating the solution with a solid adsorption material;

(b) crystallizing the protein from the solution; and (c) harvesting the crystals obtained in step (b).

2. A method according to claim 14, further comprising removing the solid adsorption material prior to step (b).

3. A method according to claim 1, wherein the concentration of protein in the solution is from 0.1 to 25% w/w.

4. A method according to claim 3, wherein the concentration of protein in the solution is from 0.5 to 15% w/w.

5. A method according to claim 4, wherein the concentration of protein in the solution is from 1 to 10% w/w.

6. A method according to claim 1, wherein the solid adsorption material is added to the solution at a concentration of 0.05–5% w/w.

7. A method according to claim 6, wherein the concentration of the solid adsorption material is 0.1–2% w/w.

8. A method according to claim 1, wherein the solid adsorption material is selected from the group consisting of an activated carbon material, diatomaceous earth, Fuller's earth, bentonite, a hydrophobic resin, an ion-exchange resin, and combinations of any of the foregoing.

9. A method according to claim 8, wherein the solid adsorption material is an activated carbon material.

10. A method according to claim 1, wherein the protein to be crystallized is an enzyme.

11. A method according to claim 10, wherein the enzyme is selected from the group consisting of a protease, a lipase, a cellulase, an amylase, and an oxidoreductase.

12. A method according to claim 1, wherein the pH of the protein solution is between 3 and 10.

13. A method according to claim 1, further comprising redissolving the crystals after harvest and removing the solid adsorption material.

14. A method according to claim 1, wherein the treating step comprises contacting the solution with the solid adsorption material in a column or filter.

15. A method according to claim 1, wherein the protein solution is obtained from a fermentation broth.

16. A method according to claim 15, wherein, prior to step (a), the fermentation broth is purified by centrifugation, filtration, microfiltration, ultrafiltration, precipitation, evaporation, or a combination thereof.

17. A method according to claim 15, wherein, prior to step (a), one or more flocculating agents are added to the fermentation broth.

* * * * *